(12) United States Patent
Annibali

(10) Patent No.: US 7,091,032 B2
(45) Date of Patent: Aug. 15, 2006

(54) **EXPRESSION OF A HUMAN INSULIN PRECURSOR IN *P. PASTORIS***

(75) Inventor: Nestor Annibali, Buenos Aires (AR)

(73) Assignee: Laboratorios Beta S.A., Buenos Aires (AR)

( * ) Notice: Subject to any disclaimer, the term of this patent is extended or adjusted under 35 U.S.C. 154(b) by 670 days.

(21) Appl. No.: 09/955,259

(22) Filed: Sep. 12, 2001

(65) Prior Publication Data

US 2003/0104607 A1 Jun. 5, 2003

(30) Foreign Application Priority Data

Sep. 13, 2000 (AR) .............................. P000104797

(51) Int. Cl.
- C12N 1/10 (2006.01)
- C12N 1/14 (2006.01)
- C12N 1/16 (2006.01)
- C12N 1/19 (2006.01)
- C12N 15/63 (2006.01)

(52) U.S. Cl. .............................. 435/254.23; 435/254.1; 435/254.11; 435/254.2

(58) Field of Classification Search .................. 435/41, 435/69.1, 69.4, 440, 471, 243, 254.1, 254.11, 435/254.2, 254.21, 254.22, 254.23, 255.1, 435/255.4, 255.5, 255.6

See application file for complete search history.

(56) References Cited

U.S. PATENT DOCUMENTS

| | | | |
|---|---|---|---|
| 4,343,898 | A | 8/1982 | Markussen |
| 4,431,740 | A | 2/1984 | Bell et al. |
| 4,916,212 | A | 4/1990 | Markussen et al. |
| 5,324,639 | A * | 6/1994 | Brierley et al. ............ 435/69.4 |
| 5,460,954 | A | 10/1995 | Lee et al. |
| 5,618,913 | A | 4/1997 | Brange et al. |
| 5,663,291 | A | 9/1997 | Obermeier et al. |
| 5,955,349 | A * | 9/1999 | Raymond ............... 435/254.23 |

FOREIGN PATENT DOCUMENTS

| | | | |
|---|---|---|---|
| EP | 0 055 945 | | 7/1982 |
| EP | 0 195 691 | | 9/1986 |
| EP | 0 195 691 A1 * | | 9/1986 |
| WO | WO 200118052 A1 * | | 3/2001 |

OTHER PUBLICATIONS

Brange et al., "Monomeric insulins obtained by protein engineering and their medical implications", Nature, vol. 333, pp. 679-682, 1988.

Castellanos-Serra et al., "Expression and folding of an interleukin-2-proinsulin fusion protein and its conversion into insulin by a single step enzymatic removal of the C-peptide and the N-terminal fused sequence", FEBS Letters 378, pp. 171-176, 1996.

Cowley et al., "Expression, purification and characterization of recombinant human proinsulin", FEBS Letters 402, pp. 124-130, 1997.

Chan et al., "Biosynthesis and periplasmic segregation of human proinsulin in *Escherichia coli*", Proc. Natnl. Acad. Sci USA vol. 78, No. 9, pp. 5401-5405, 1981.

Chance et al., "Chemical, Physical, and Biologic Properties of Biosynthetic Human Insulin", Diabetes care, vol. 4, No. 2, pp. 147-154, 1981.

Chance et al., "The Production of Human Insulin Using Recombinant DNA Technology and a New Chain Combination Procedure", Diabetes care 4:147; pp. 721-728, 1981.

Chang et al., "Human insulin production from a novel mini-proinsulin which has high receptor-binding activity", Biochem. J. 329, pp. 631-635, 1998.

Cregg et al., "Functional Characterization of the Two Alcohol Oxidase Genes from the Yeast *Pichia pastoris*", Molecular and Cellular Biology, vol. 9, No. 3, pp. 1316-1323, 1989.

Cregg et al., "Recent Advances in the Expression of Foreign Genes in *Pichia pastoris*", Bio/Technology vol. 11, pp. 905-910, 1993.

Di Donato et al., "A Method for Synthesizing Genes and cDNAs by the Polymerase Chain Reaction", Analytical biochemistry, 212, pp. 291-293, 1993.

Frank et al., "The Production of Human Proinsulin and its Transformation to Human Insulin and C-Peptide", Proceedings of the 7$^{th}$ Am Peptide Chem. Symposium, pp. 729-738, 1981.

Gagnon et al., "Large-Scale Process Development for Hydrophobic Interaction Chromatography, Part 1: Gel Selection and Development of Binding Conditions", Biopharm 8, pp. 21-27, 1995.

Goeddel et al., "Expression In *Escherichia coli* of chemically synthesized genes for human insulin", Proc. Natnl. Acad. Sci. USA vol. 76, No. 1, pp. 106-110, 1979.

Jensen et al., "Scintigraphic Studies in Rats", Diabetes, vol. 40, pp. 628-632, 1991.

Katsoyannis et al., "Studies on the Synthesis of Insulin from Natural and Synthetic A and B Chains. I. Splitting of Insulin and Isolation of the S-Sulfonated Derivatives of the A and B Chains", Am. Chem. Soc. vol. 6, No. 9, pp. 2635-2655, 1967.

Kemmler et al., "Studies on the Conversion of Proinsulin to Insulin", The J. of Biol. Chem. vol. 246, No. 22, pp. 6786-6791, 1971.

Kristensen et al., "Alanine Scanning Mutagenesis of Insulin", The J. of Biol. Chem. vol. 272, No. 20, pp. 12978-12983, 1997.

(Continued)

Primary Examiner—David Guzo
Assistant Examiner—Michele K. Joike
(74) Attorney, Agent, or Firm—Squire, Sanders & Dempsey, L.L.P.

(57) ABSTRACT

Methylotrophic recombinant yeast strain producing human insulin precursor, the strain comprising, in its genome, a copy of a first DNA construction and a second DNA construction, wherein the constructions are capably of directing the expression and secretion of human insulin precursor of the formula B(1-30)-Y1-Y2-A(1-21), wherein Y1 is lysine or arginine; Y2 is lysine or arginine; B(1-30) is the B peptide of the human insulin; and B(1-21) is the A peptide of human insulin, and wherein the strain is yeast *Pichia Pastoris*. DNA constructions and method for obtaining the strain are also provided.

1 Claim, 2 Drawing Sheets

OTHER PUBLICATIONS

Kroeff et al., "Production Scale Purification of Biosynthetic Human Insulin by Reversed-Phased High-Performance Liquid Chromatography", J. of Chromatography, 461, pp. 45-61, 1989.

Rose et al., "Rapid preparation of human insulin and insulin analogues in high yield by enzyme-assisted semi-synthesis", Biochem. J. 211, pp. 671-676, 1983.

Smith et al, "Heterologous Protein Secretion from Yeast", Science, vol. 229, pp. 1219-1224, 1985.

Steiner et al., "The Spontaneous Reoxidation of Reduced Beef and Rat Proinsulins", Biochemistry: Steiner and Clark, vol. 60, pp. 622-629, 1968.

Thim et al., "Secretion and processing of insulin precursors in yeast", Proc. Natnl. Acad. Sci. USA vol. 83, pp. 6766-6770, 1986.

Veenhuis et al., "The Significance of Peroxisomes in the Metabolism of One-Carbon Compounds in Yeasts", Advances in Microbial Physiology, vol. 24, 81 pgs. 1983.

Wang et al., "Studies on Receptor Binding Site of Insulin: The Hydrophobic B12VAL Can be Substituted by Hydrophilic THR", Biochem. and Molecular Biol. International vol. 39, No. 6 pp. 1245-1254, 1996.

Wollmer et al., "Reduction/Reoxidation Studies with Cross-Linked Insulin Derivatives", Hoppe-Seyler's Z. Physiol. Chem. Bd. 355, pp. 1471-1476, 1974.

* cited by examiner

SEQUENCE LISTING

<160> NUMBER OF SEQ ID NOS: 26

<210> SEQ ID NO 1
<211> LENGTH: 36
<212> TYPE: DNA
<213> ORGANISM: Artificial Sequence
<220> FEATURE:
<223> OTHER INFORMATION: Synthetic Primer

<400> SEQUENCE: 1
tcacacctgg tggaagctct ctacctagtg tgcggg    36

```
<210> SEQ ID NO 2
<211> LENGTH: 45
<212> TYPE: DNA
<213> ORGANISM: Artificial Sequence
<220> FEATURE:
<223> OTHER INFORMATION: Synthetic Primer

<400> SEQUENCE: 2
ggtcttgggt gtgtagaaga agcctcgttc cccgcacact aggta                45

<210> SEQ ID NO 3
<211> LENGTH: 39
<212> TYPE: DNA
<213> ORGANISM: Artificial Sequence
<220> FEATURE:
<223> OTHER INFORMATION: Synthetic Primer

<400> SEQUENCE: 3
tttgtgaacc aacacctgtg cggctcacac ctggtggaa                       39

<210> SEQ ID NO 4
<211> LENGTH: 45
<212> TYPE: DNA
<213> ORGANISM: Artificial Sequence
<220> FEATURE:
<223> OTHER INFORMATION: Synthetic Primer

<400> SEQUENCE: 4
gctggtacag cattgttcca caatgccacg cttggtcttg ggtgt                45

<210> SEQ ID NO 5
<211> LENGTH: 52
<212> TYPE: DNA
<213> ORGANISM: Artificial Sequence
<220> FEATURE:
<223> OTHER INFORMATION: Synthetic Primer

<400> SEQUENCE: 5
ctagttgcag tagttctcca gctggtagag ggagcagatg ctggtacagc at         52

<210> SEQ ID NO 6
<211> LENGTH: 162
<212> TYPE: DNA
<213> ORGANISM: Artificial Sequence
<220> FEATURE:
<223> OTHER INFORMATION: complete synthetic insulin precursor obtained
      by PCR using human insulin sequence as original source

<400> SEQUENCE: 6
tttgtgaacc aacacctgtg cggctcacac ctggtggaag ctctctacct agtgtgcggg   60
gaacgaggct tcttctacac acccaagacc aagcgtggca ttgtggaaca atgctgtacc  120
agcatctgct ccctctacca gctggagaac tactgcaact ag                    162

<210> SEQ ID NO 7
<211> LENGTH: 50
<212> TYPE: DNA
<213> ORGANISM: Artificial Sequence
<220> FEATURE:
<223> OTHER INFORMATION: Synthetic Primer

<400> SEQUENCE: 7
acttggttga agctttgtac ttggtttgtg gtgaaagagg tttcttctac             50

<210> SEQ ID NO 8
<211> LENGTH: 50
```

```
<212> TYPE: DNA
<213> ORGANISM: Artificial Sequence
<220> FEATURE:
<223> OTHER INFORMATION: Synthetic Primer

<400> SEQUENCE: 8
agaagtacaa cattgttcaa cgatacctct cttagtcttt ggagtgtaga                 50

<210> SEQ ID NO 9
<211> LENGTH: 33
<212> TYPE: DNA
<213> ORGANISM: Artificial Sequence
<220> FEATURE:
<223> OTHER INFORMATION: Synthetic Primer

<400> SEQUENCE: 9
acacttgtgt ggttctcact tggttgaagc ttt                                   33

<210> SEQ ID NO 10
<211> LENGTH: 66
<212> TYPE: DNA
<213> ORGANISM: Artificial Sequence
<220> FEATURE:
<223> OTHER INFORMATION: Synthetic Primer

<400> SEQUENCE: 10
ttactcgagt tagttacagt agttttccaa ttggtacaaa gaacagatag aagtacaaca      60
ttgttc                                                                 66

<210> SEQ ID NO 11
<211> LENGTH: 36
<212> TYPE: DNA
<213> ORGANISM: Artificial Sequence
<220> FEATURE:
<223> OTHER INFORMATION: Synthetic Primer

<400> SEQUENCE: 11
ccgctcgaga agagatttgt taaccaacac ttgtgt                                36

<210> SEQ ID NO 12
<211> LENGTH: 162
<212> TYPE: DNA
<213> ORGANISM: Artificial Sequence
<220> FEATURE:
<223> OTHER INFORMATION: synthetic insulin precursor, obtained by PCR
      using human insulin sequence as original source

<400> SEQUENCE: 12
tttgttaacc aaacacttgtg tggttctcac ttggttgaag ctttgtactt ggtttgtggt     60
gaaagaggtt tcttctacac tccaaagact aagagaggta tcgttgaaca atgttgtact     120
tctatctgtt ctttgtacca attggaaaac tactgtaact aa                        162

<210> SEQ ID NO 13
<211> LENGTH: 56
<212> TYPE: DNA
<213> ORGANISM: Artificial Sequence
<220> FEATURE:
<223> OTHER INFORMATION: Synthetic Primer

<400> SEQUENCE: 13
cgcggatcca aaccatgaga ttcccatcta tcttcactgc tgttttgttc gctgct         56

<210> SEQ ID NO 14
<211> LENGTH: 68
```

```
<212> TYPE: DNA
<213> ORGANISM: Artificial Sequence
<220> FEATURE:
<223> OTHER INFORMATION: Synthetic Primer

<400> SEQUENCE: 14
gttttgttcg ctgcttcttc tgctttggct gctcctgtta acactactac tgaagacgaa      60
actgctca                                                                68

<210> SEQ ID NO 15
<211> LENGTH: 71
<212> TYPE: DNA
<213> ORGANISM: Artificial Sequence
<220> FEATURE:
<223> OTHER INFORMATION: Synthetic Primer

<400> SEQUENCE: 15
acgtcgaagt caccttccaa gtcagagtaa ccgataaccg cttcagctgg gatttgagca      60
gtttcgtctt c                                                           71

<210> SEQ ID NO 16
<211> LENGTH: 66
<212> TYPE: DNA
<213> ORGANISM: Artificial Sequence
<220> FEATURE:
<223> OTHER INFORMATION: Synthetic Primer

<400> SEQUENCE: 16
gatgaacaac aaaccattat tagtagagtt agagaaaggc aaaacagcaa cgtcgaagtc      60
accttc                                                                 66

<210> SEQ ID NO 17
<211> LENGTH: 72
<212> TYPE: DNA
<213> ORGANISM: Artificial Sequence
<220> FEATURE:
<223> OTHER INFORMATION: Synthetic Primer

<400> SEQUENCE: 17
ccgctcgaga gaaacaccct cttccttagc agcgatagaa gcgatagtag tgttgatgaa      60
caacaaacca tt                                                          72

<210> SEQ ID NO 18
<211> LENGTH: 267
<212> TYPE: DNA
<213> ORGANISM: Artificial Sequence
<220> FEATURE:
<223> OTHER INFORMATION: synthetic sequence of alpha factor from S.
      cerevisiae, obtained by PCR

<400> SEQUENCE: 18
atgagattcc catctatctt cactgctgtt ttgttcgctg cttcttctgc tttggctgct      60
cctgttaaca ctactactga agacgaaact gctcaaatcc cagctgaagc ggttatcggt     120
tactctgact ggaaggtgac ttcgacgtt gctgttttgc cttctctaa ctctactaat       180 aatggttttgt tgttcatcaa cactactatc gcttctatcg ctgctaagga agagggtgtt    240
tctctcgaga agagagaggc tgaagca                                         267

<210> SEQ ID NO 19
<211> LENGTH: 44
<212> TYPE: DNA
<213> ORGANISM: Artificial Sequence
```

```
<220> FEATURE:
<223> OTHER INFORMATION: Synthetic Primer

<400> SEQUENCE: 19
ggggatccat atgctcgaga aaagatttgt gaaccaacac ctgt          44

<210> SEQ ID NO 20
<211> LENGTH: 32
<212> TYPE: DNA
<213> ORGANISM: Artificial Sequence
<220> FEATURE:
<223> OTHER INFORMATION: Synthetic Primer

<400> SEQUENCE: 20
ttagaattcc cgggtctagt tgcagtagtt ct                       32

<210> SEQ ID NO 21
<211> LENGTH: 30
<212> TYPE: DNA
<213> ORGANISM: Artificial Sequence
<220> FEATURE:
<223> OTHER INFORMATION: Synthetic Primer

<400> SEQUENCE: 21
tcactcgagc ggtctagttg cagtagttct                          30

<210> SEQ ID NO 22
<211> LENGTH: 28
<212> TYPE: DNA
<213> ORGANISM: Artificial Sequence
<220> FEATURE:
<223> OTHER INFORMATION: Synthetic Primer

<400> SEQUENCE: 22
gtcgtggttt ctcatagtag agtggaca                            28

<210> SEQ ID NO 23
<211> LENGTH: 18
<212> TYPE: DNA
<213> ORGANISM: Artificial Sequence
<220> FEATURE:
<223> OTHER INFORMATION: Synthetic Primer

<400> SEQUENCE: 23
ggtcatcact gctccatc                                       18

<210> SEQ ID NO 24
<211> LENGTH: 19
<212> TYPE: DNA
<213> ORGANISM: Artificial Sequence
<220> FEATURE:
<223> OTHER INFORMATION: Synthetic Primer

<400> SEQUENCE: 24
agcagcacca gtggaagat                                      19

<210> SEQ ID NO 25
<211> LENGTH: 21
<212> TYPE: DNA
<213> ORGANISM: Artificial Sequence
<220> FEATURE:
<223> OTHER INFORMATION: Synthetic Primer

<400> SEQUENCE: 25
gactggttcc aattgacaag c                                   21
```

-continued

```
<210> SEQ ID NO 26
<211> LENGTH: 4
<212> TYPE: PRT
<213> ORGANISM: Saccharomyces cerevisiae

<400> SEQUENCE: 26

Lys Arg Glu Ala
1
```

EXPRESSION OF A HUMAN INSULIN PRECURSOR IN *P. PASTORIS*

BACKGROUND OF THE INVENTION

1. Field of the Invention

The present invention relates to the expression of human insulin in *P. pastoris* and, more particularly the invention is related to the field of DNA recombinant technology and to the production of insulin precursors in host microorganisms such as yeast. More precisely, the invention refers to a recombinant methylotrophic yeast strain for producing human insulin precursors. The invention also relates to DNA constructions and methods for obtaining the strains. The inventive strain comprises, in its genome, at least one copy of a first DNA construction and one copy of a second DNA construction, wherein said constructions are capable of expressing and secreting an insulin precursor.

2. Description of the Prior Art

It is well known that diabetes is usually treated with insulin injections, e.g. of human insulin. Insulin is an essential hormone in metabolism and is a protein consisting of two polypeptide chains, namely A chain and B chain. A chain comprises 21 amino acid residues and B chain comprises 30 amino acid residues, and both chains are covalently connected by disulfide bridges in the positions A7–B7 and A20–B19, and by an intra-chain disulfide bond connecting residues A6–A11.

Insulin is produced in the pancreas by the β cells of the Langerhans islets as preproinsulin. Preproinsulin consists of a prepropeptide having 24 amino acids acting as an export signal sequence followed by a peptide named proinsulin and containing 86 amino acid residues. Said preproinsulin may be represented by: prepeptide-B-C-A, wherein the C peptide is a connecting peptide comprising 31 amino acid residues and chains A and B are chains A and B of proinsulin.

When the preproinsulin chain is synthesized, the signal peptide directs synthesis towards the endoplasmic reticulum of the β cells and at that moment the signal peptide splits out, secreting the proinsulin into the endoplasmic reticulum.

Then, during packing of the insulin molecule within the secreting system of the β cells, the C peptide is cleaved, thus liberating the native insulin molecule, which is appropriately "folded". Cleavage of the C peptide is carried out through the action of enzymes acting upon the proinsulin dibasic sequences.

Presently it is known that the C peptide has an important function in the formation of the tertiary structure of the insulin molecule.

The production of insulin for treating diabetes has been a concern in the pharmaceutical industry for many years. Since the development of recombinant DNA techniques, a wide variety of methods for the production of insulin in microorganisms have been published.

Bacteria were the first host microorganisms employed in recombinant DNA techniques, particularly *Escherichia coli* (*E. coli*). In the first experiments using *E. coli*, strategies similar to those used in the production of synthetic insulin were employed. According to these methods, chains A and B were cloned and expressed independently in the host microorganisms, thus obtaining two polypeptides corresponding to chains A and B. The native insulin was then obtained by performing the steps of forming disulfide bonds between chains A and B and the respective intra-chain bridge in vitro. This oxidizing process was carried out as described by Chance, R. E. et al., in Diabetes Care 4:147; 1981; and Goedel, D. V. et al. in Proc. Natl. Acad. Sci. U.S.A. 76: 106–110, 1979. One of the biggest difficulties presented by this method was the random formation of disulfide bonds, which generated molecules with an incorrect tertiary structure. Through this method, the yield of native insulin with biological activity was extremely low, thus increasing production costs dramatically.

In view of the above difficulties, experts have introduced the idea of cloning the DNA sequence of proinsulin or its derivatives, where the C peptide is represented by fragments of different sizes. This idea is based on the fact that the presence of the C peptide or its derivatives produces a higher yield of correctly folded proinsulin after the oxidizing step as compared to the yield resulting from oxidizing chains A and B separately (Dteiner, D. F. et al. Proc. Acad. Sci. 60:622; 1968). Thus, it was observed that chain C which acts as a connecting peptide of chains B and A, allows for cysteine residues to be spatially favored for a correct oxidation. It was demonstrated that the proinsulin molecule formed in this manner could function as a precursor from which insulin could be obtained by in vitro removal of peptide C, using specific enzymes. (Kemmler, W. et al. J. Biol. Chem. 91: 246:6786; 1971). It was also demonstrated that if fragment C of these precursors was changed for a connecting peptide of a smaller size that maintains in vitro cleavable sites at both ends, and, if proper enzyme action was used, equivalent, and in some cases better results were obtained in the production of insulin. These precursors were named mini-proinsulins (Wollmer, A. et al. Hoppe-Seyler's, Z. Physiol. Chem. 355:1471–1476; 1974 and EPO Patent 195 691).

European Patent No. EP 0055945 discloses a process for producing and expressing proinsulin in *E. coli* and methods for producing human insulin. The production of proinsulin in *E. Coli* on a large or commercial scale is disclosed in U.S. Pat. No. 5,460,954. U.S. Pat. No. 4,431,740 discloses a DNA having a sequence encoding proinsulin, and another DNA encoding pre-proinsulin, and a microorganism such as *E. coli* transformed with such sequences.

However, the expression of heterologous proteins in *E. coli*, has a number of difficulties well known by those skilled in the art. Briefly, the following can be mentioned:

When an *E. coli* or any prokaryotic microorganism is used as a host for the expression of proteins from eukaryotes, the microorganism is incapable of forming the disulfide bonds which allow for the correct formation of a tertiary structure. As a consequence, when proteins such as human insulin are cloned and expressed in microorganisms, said proteins tend to aggregate forming inactive complexes or inclusion bodies.

Solubilization and purification of proinsulin from the inclusion bodies requires a large number of additional steps. One of these steps comprises dissolving the aggregates with reagents such as urea or guanidine chloride. Subsequently, it is necessary to submit the insulin precursor to an oxidizing agent by oxidative sulfitolysis, wherein the cysteine molecules of both chains adopt the $SSO^-_3$ form. Subsequently, the S-sulfonated groups are converted into sulphydryl groups (—SH—) in the presence of a thiolated agent (dithiotreitol or 2-mercaptoethanol). Finally, these groups are oxidized in presence of oxygen for the formation of the sulfide bonds.

New methods for the recovery of proinsulin from the inclusion bodies are still the aim of several investigations, attempting to improve the yield and achieve a correct folding of the protein which is dramatically reduced by purification of the protein and causes the purification process to be extremely complex. (Chance, R. et al. Proceedings of the Seventh American Peptide Chemistry Symposium, pages 721–728; 1981; Pierce Chemical Company, Rockford, Ill.; Chan, S. J. et al. Proc. Natl. Acad. Sci. USA 78 (9): 5401–5405, 1981, and Frank, B. H. et al. Proceedings of the Seventh American Peptide Chemistry Symposium, pages 729–739; 1981; Pierce Chemical Company, Rockford, Ill.).

In addition, in *E. coli* or any other prokaryote organisms protein translation starts with a methionine residue. In order to remove the methionine from the amino terminal end the gene of interest is usually cloned as a fusion protein. The removal of insulin from the fusion peptide requires an additional step involving digestion of the peptide with specific proteases. Otherwise, the methionine residue must be removed with cyanogen bromide (CNBr).

European Patent No. 0 055 945 discloses a method and a vector to cleave a proinsulin analog having a smaller C peptide and wherein the methionine residue is removed by treatment with CNBr.

Other difficulties and drawbacks that may be found in the expression of heterologous proteins in prokaryotes is the decrease or reduction of protein stability under the action of cytoplasmic protease. U.S. Pat. No. 5,460,954 discloses a process for producing human proinsulin in *E. coli* which comprises a vector containing a sequence at the 5' end of the proinsulin gene, encoding an amino acid sequence which prevents degradation by protease within the cell.

Many investigators are attempting to improve the methods for producing human insulin in *E. coli* through a simpler method and with better results. These methods for improving protein yield consist in replacing the C peptide by smaller sequences (Chang, Seung-Gu at al. *Biochem. J.* 329; 631–635, 1998).

Methods for expressing proinsulin in bacteria have also been developed, which combine different procedures such as the expression of a fusion protein comprising a polyhistidine tail in the N-terminal end, a methionine residue and the proprotein sequence of of human insulin, all included in an expression vector for bacteria (Cowley, Darrin J. et al. FEBS Letters, 402: 124–130, 1997).

By reason of the operative drawbacks and difficulties found in the expression of human insulin in prokaryotic hosts, many attempts have been made to obtain high levels of expression of human insulin in eukaryotic hosts such as yeast. Consequently, yeast has become one of the selected hosts for the expression of eukaryotic proteins. These microorganisms provide clear advantages as compared to bacteria in relation to the production of mammalian proteins. Yeast has secretion mechanisms that are similar to those of mammals and has the capacity of properly folding, proteolitically processing, glycosilating and secretingmammalian proteins.

When appropriate vectors are employed in the yeast for exporting the protein outside the cell, the process for recovering and purifying the proteins exported into the culture medium is simpler and has a better yield than the expression in cell cytoplasm. In addition, the secretion system provides an appropriate environment for the formation of the di-sulfide bonds that are necessary for protein folding (Smith, et al. 1985; *Science* 229:1219). On the other hand, cytoplasm is a reducing environment in which these bonds are not formed. Under these circumstances, production of any proteins requiring di-sulfide bonds for maintaining a correct tertiary structure, as is the case of insulin, will have better results when said proteins are secreted.

A yeast system used as host for the production of a large number of proteins is, for example, the yeast species *Saccharomyces cerevisiae*. The genetic structure of this yeast has been studied in detail by a number of investigation groups.

Several polypeptides such as insulin have been cloned and expressed in *Saccharomyces cerevisiae*. The expression of this propeptide may follow the secretory path or may be accumulated in the cytoplasm of the host microorganism. In the event of the accumulation, time consuming and complex purification processes must be employed, the processes requiring steps for the formation of di-sulfide bonds, as disclosed in European Patent No. 37255. In order to avoid these drawbacks and complicated steps, the proinsulin gene sequence is cloned subsequently to an additional DNA sequence named "leader" or signal peptide that originates the pre-proinsulin peptide. This peptide, once recognized and processed by the yeast, provides the secretion of pro-insulin into the culture medium.

In addition to the foregoing, any precursors of the proinsulin type that are produced in *Saccharomyces cerevisiae* undergo a rapid enzymatic process either when expressed in the cytoplasm or when secreted into the medium. It has been demonstrated that human proinsulin is especially sensitive to enzymatic cuts in two dibasic sequences ($Arg_{31}$–$Arg_{32}$ and $Lys_{64}$–$Arg_{65}$). This causes the cleavage of the molecule before the formation of the di-sulfide bonds, thus resulting in the separate generation of peptides C, A and B.

It has been found that if, instead of proinsulin, shorter sequences are employed wherein the C peptide has been removed or, it is simply represented by shorter fragments having up to two amino acids of lysine, arginine type, a more stable molecule is obtained, which is not digestible by proteases, and capable of been processed in vitro to give a biologically active insulin molecule (Lars Thim et al. Proc. Natl. Acad. Sci. USA 83: 6766–67770; 1986).

European Patent No. 195 691 discloses several precursors, inter alia, those of type B-X-Y-A where B and A correspond to the B and A chains of human insulin, and where X and Y are represented by the amino acids lysine and arginine, these amino acids being digestible by the trypsine and carboxypeptidase B enzymes for their conversion into human insulin. However, while considerable amounts of $A_0$Arg-desB(30) are produced as digestion sub-products, these sub-products do not have amino acid 30 of the B chain while an arginine residue remains connected to the A chain. The arginine residue can not be easily removed and this causes serious inconveniencies in the process of purifying the protein, also considerably diminishing product yields. Total yield of this precursor in *Saccharomyces cerevisiae* is remarkably low.

On the other hand, U.S. Pat. No. 4,916,212 discloses a simple chain proinsulin precursor, where said precursor is represented by the formula: $B_{(1-29)}$—$(X_n$—$Y)_m$—$A_{(1-21)}$, $X_n$ is a peptidic chain of n amino acids, Y is lysine or arginine, n is an integer from 0 to 35, m is 0 or 1, $B_{(1-29)}$ is a B chain lacking the threonine at position 30, and $A_{(1-21)}$ is the A chain of human insulin. This US patent reveals that —$X_n$—Y— does not have two adjacent basic amino acids, such as lysine and arginine, because the digestion with trypsin produces byproducts that are difficult to separate during the purification steps. The products obtained from these genetic designs do not contain threonine at position 30 and, therefore, they must be subjected to an additional step consisting in the addition of this amino acid by the catalytic action of trypsin in the presence of Thr-Obu ester, as disclosed in U.S. Pat. No. 4,343,898 and Rose, K. et al. *Biochem. J.* 211: 671–676, 1983.

In any case, in addition to all the modifications introduced into the insulin precursors, the expression of these peptides in *Saccharomyces cerevisiae* has resulted in low yields and scaling drawbacks in heterologous protein production. These problems are generally associated to low efficiency promoters and to the fact that the sequences of interest are cloned in autonomous replication plasmids. These plasmids do not remain uniformly distributed within the culture medium and they usually decrease as the number of copies increases. As a result of this, and after some duplication cycles, cells with 2, 3 or 0 copies of the plasmid used as vector are found in the culture (Chan, S. J. et al. *Proc. Natl. Acad. Sci. USA* 78 (9): 5401–5405. 1981).

An expression system in yeast, but not using *Saccharomyces* as a host, is the methylotrophic yeast system. These microorganisms may be very useful as hosts for the expression of heterologous proteins required to be produced in large volumes. Heterologous proteins that are expressed in methylotrophic yeast may be secreted with expression levels that are equivalent to those of *E. coli* and higher than those of *Saccharomyces cerevisiae*.

Mthylotrophic yeasts are unicellular microorganisms capable of growing in the presence of methanol as the only carbon source. This yeast can be kept without trouble in high cellular densities when grown in a high volume fermentor. In addition, this yeast is capable of producing many of the post-translated modifications undergone by the higher eukaryotic cells, such as proteolytic digestions, protein folding, di-sulfide bonds formation and glycosilation.

*Pichia pastoris* is one of the twelve species within the four yeast genera capable of metabolizing methanol as the only one carbon source (Cregg, J. M. et al. *Bio/Technology* 11:905–910, 1993). The remaining genera are represented by *Candida*, *Hansenula* and *Torulopsis*.

These yeasts share a large number of enzymes corresponding to the metabolic pathways of methanol (Veenhuis, M. et al. *Adv. Microb. Physiol.* 24:1–82, 1983). The first step of this metabolic pathway is the oxidation of methanol into formaldehyde, generating hydrogen peroxide by action of the alcohol oxidase enzyme (AOX).

The cell avoids hydrogen peroxide toxicity by carrying out this first metabolic reaction of methanol in a special organelle named peroxisome.

There are two genes in *P. pastoris* which encode alcohol oxidase enzymes I and II: AOX1 and AOX2 genes. The AOX2 gene is responsible of most alcohol oxidase activity in the cell (Cregg, J. M. et al. *Mol. Cell. Biol.* 9:1316–1323, 1989).

The expression of this gene is highly regulated and it is induced by methanol, with AOX1 representing a value close to 30% of the total soluble cell proteins. It is for this reason that the expression systems usually employed with *Pichia pastoris* include in their vectors the AOX1 gene promoter.

Thomas Kjeldsen et al. compared the expression of proinsulin and precursor peptides of ($B_{1-29}$-Ala-Ala-Lys-$A_{1-21}$) insulin in *S. cereviciae* and in *P. pastoris*. The products were secreted into the culture medium with the aid of an amino acid sequence that is fused to the leader (amino) end of the precursor. Several signal peptides were employed for determining the secretion efficiency of the insulin precursor such as the pre-pro-peptide αmating factor of *Saccharomyces cerevisiae* and synthetic derivatives thereof. These pre pro peptides have amino acid sequences useful as targets for the activity of specific proteases resulting in the release of the peptide into the culture medium. All the insulin peptides employed by these authors are secreted into the medium as a precursor lacking threonine at position 30 of the B chain.

This product, recovered and purified from the culture medium, had to be submitted to an exhaustive process called transpeptidation. Transpeptidation consists in the addition of threonine and it is disclosed in U.S. Pat. No. 4,916,212 to Markussen et al. It adds a step to the purification process of the insulin molecule.

In the above described state of the art, it has been a concern of the inventors to find a solution to all of the above mentioned problems and drawbacks in the prior art.

SUMMARY OF THE INVENTION

It is therefore one object of the present invention to provide a new yeast strain capable of producing and secreting into the medium an insulin precursor in proper quantities useful for industrial application, wherein the inventive strain comprises two distinct DNA constructions for expressing a DNA sequence encoding an insulin precursor. Said gene is cloned in such a way that an insulin precursor is secreted into the medium, said insulin precursor containing at its terminal end a first amino acid of the insulin B-chain, thus avoiding the steps of removing the remaining amino acids from the signal peptide.

It is a further object of the present invention to provide a methylotrophic recombinant yeast strain for producing human insulin precursor, the strain having a genome comprising a copy of a first DNA construction and a second DNA construction, wherein said constructions control the expression and secretion of a human insulin precursor, said DNA constructions comprising at least one DNA sequence encoding a human insulin precursor or analogues thereof.

It is even another object of the present invention to provide a yeast strain comprising in its genome DNA constructions capable of expressing a human insulin precursor of the formula:

B(1-30)-Y1-Y2-A(1-21), wherein Y1 is lysine or arginine; Y2 is lysine or arginine; B(1-30) is the B peptide of human insulin; and B(1-21) is the A peptide of human insulin.

It is even another object of the present invention to provide a *Pichia pastoris* strain deposited on Jul. 25, 2000, with American Type Culture Collection (ATCC) under accession number PTA-2260, wherein the yeast strain comprises, in its genome, a first DNA construction comprising:
a) a first insertion DNA sequence corresponding to a 5' regulatory region of *Pichia pastoris* AOX1 gene, operably linked to
b) the MF α signal sequence of *Sacharomyces cerevisiae*, operably linked to
c) the sequence encoding a human insulin precursor, preferably a precursor of formula B(1-30)-Y1-Y2-A(1-21) operably linked to
d) a 3' transcription termination sequence of *Pichia pastoris* AOX1 gene operably linked to
e) a *Pichia pastoris* HIS4 selectable gene operably linked to
f) a second insertion sequence corresponding to the 3' end of the *Pichia pastoris* AOX1 gene; and
a second DNA construction comprising:
a) a first insertion DNA sequence corresponding to a 5' regulatory region of *Pichia pastoris* AOX1 gene operably linked to
b) the MF α signal sequence of *Sacharomyces cerevisiae* operably linked to
c) the sequence encoding a human insulin precursor, preferably a precursor of formula B(1-30)-Y1-Y2-A(1-21) operably linked to d) a 3' transcription termination sequence of the *Pichia pastoris* AOX1 gene operably linked to e) the zeocine-resistant selectable gene.

It is still another object of the present invention to provide a first DNA construction comprising at least one expression cassette for expressing the human insulin precursor, the cassette comprising:

a) a 5' regulatory region operably linked to b) a DNA sequence encoding a signal sequence operably linked to c) a sequence encoding a human insulin precursor operably linked to d) a functional 3' transcription termination sequence.

According to an embodiment of the invention, the first DNA construction comprises, at its 5' and 3' ends, sequences with sufficient homology to a target gene of the yeast to permit the insertion by gene replacement of the DNA construction in the target gene, in the same relative sense of the target gene in the yeast genome, these 5' and 3' sequences that are homologous to the target gene being sequences flanking the expression cassette.

It is even another object of the present invention to provide a first DNA construction, further comprising:

a) a first insertion DNA sequence corresponding to a 5' regulatory region of *Pichia pastoris* AOX1 gene operably linked to b) the MF α signal sequence of *Sacharomyces cerevisiae* operably linked to c) the sequence encoding a human insulin precursor, preferably a precursor of formula B(1-30)-Y1-Y2-A(1-21) operably linked to d) a 3' transcription termination sequence of *Pichia pastoris* AOX1 gene operably linked to e) a *Pichia pastoris* HIS4 selectable gene operably linked to f) a second insertion sequence corresponding to the 3' sequence of the *Pichia pastoris* AOX1 gene.

It is a further object of the present invention to provide a second DNA construction comprising at least one expression cassette for expressing a human insulin precursor, the cassette comprising:

a) a 5' regulatory region operably linked to b) a DNA sequence encoding a signal sequence operably linked to c) a sequence encoding a human insulin precursor operably linked to d) a functional termination sequence.

According to a preferred embodiment of the invention, the second DNA construction comprises a selection marker gene distinct from the selection marker gene of the first DNA construction, thus permitting a second selection of the inventive transformed yeast strain.

According to another embodiment of the invention, the second DNA construction comprises a single sequence homologous enough with a target gene of yeast, allowing the integration of the DNA construction into the target gene, in a single event.

It is even another object of the present invention to provide a second DNA construction comprising:

a) a first insertion DNA sequence corresponding to a 5' regulatory region of *Pichia pastoris* AOX1 gene operably linked to b) the MF α signal sequence of *Sacharomyces cerevisiae* operably linked to c) the sequence encoding a human insulin precursor, preferably a precursor of formula B(1-30)-Y1-Y2-A(1-21) linked to d) a 3' transcription termination sequence of *Pichia pastoris* AOX1 gene linked to e) a zeocine-resistant selectable gene.

According to an embodiment of the invention, in both DNA constructions, the sequence encoding the human insulin precursor is cloned in said construction in a position adjacent to the protease site, wherein all the secreted human insulin precursor contains, in its amino terminal region, the phenylalanine amino acid.

Also according to an embodiment of the invention, each of the DNA constructions is incorporated into a vector selected from the group consisting of linear and circular vectors.

It is even another object of the present invention to provide a method of obtaining a transformed methylotrophic yeast strain for producing high quantities of a human insulin precursor, the method comprising the steps of:

i) transforming a yeast cell with a first DNA construction comprising:

a) a first insertion DNA sequence corresponding to a 5' regulatory region of *Pichia pastoris* AOX1 gene operably linked to b) the MF α signal sequence of *Sacharomyces cerevisiae* operably linked to c) the sequence encoding a human insulin precursor, preferably a precursor of formula B(1-30)-Y1-Y2-A(1-21) operably linked to d) a 3' transcription termination sequence of the *Pichia pastoris* AOX1 gene operably linked to e) a *Pichia pastoris* HIS4 selectable gene operably linked to f) a second insertion sequence corresponding to the 3' end of the *Pichia pastoris* AOX1 gene;

ii) selecting the yeast cells;

iii) isolating a yeast strain;

iv) re-transforming the yeast strain obtained in steps i)–iii) with a second DNA construction comprising:

a) a first insertion DNA sequence corresponding to a 5' regulatory region of the *Pichia pastoris* AOX1 gene operably linked to b) the MF α signal sequence of *Sacharomyces cerevisiae* operably linked to c) a sequence encoding a human insulin precursor, preferably a precursor of formula B(1-30)-Y1-Y2-A(1-21) linked to d) a 3' transcription termination sequence of the *Pichia pastoris* AOX1 gene linked to e) the zeocine-resistant selectable gene;

v) selecting the re-transformed yeast strain; and vi) isolating the selected and re-transformed yeast strain.

It is still another object of the present invention to provide an insulin precursor secreted into the medium as a precursor containing threonine at position 30 of B chain, thus avoiding the complex and cumbersome transpeptidation step.

The above and other objects, features and advantages of this invention will be better understood when interpreted in connection with the accompanying drawings and description thereof.

BRIEF DESCRIPTION OF THE DRAWINGS

The present invention is illustrated by way of example with the following drawings where.

DESCRIPTION OF THE PREFERRED EMBODIMENTS

Figure 1:
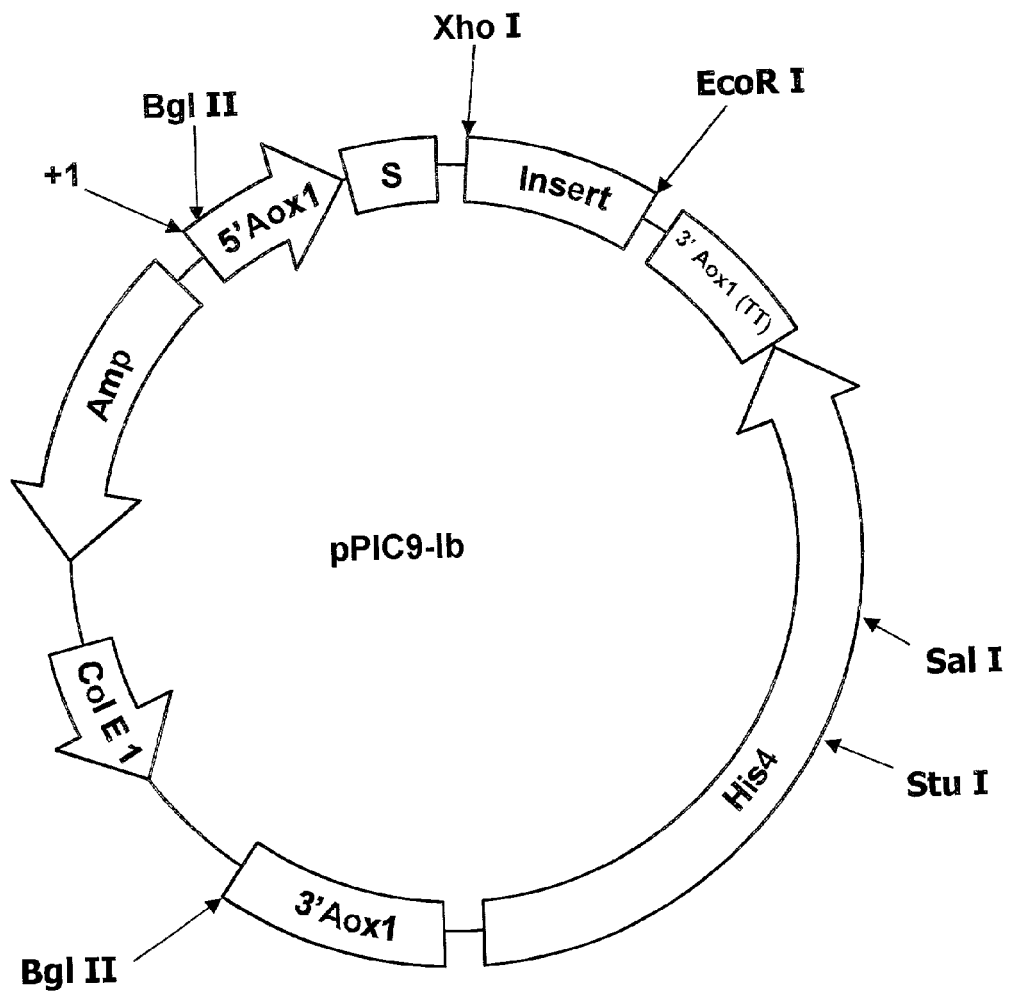
FIG. 1 shows a restriction map of plasmid pPIC9-Ib.

Unless otherwise defined herein, the technical and scientific terminology used in the present description has the meaning commonly understood by the person skilled in the art. All patents and publications mentioned in the present application are incorporated herein by reference only.

Definitions

The term "human insulin precursor" or "proinsulin" as used herein refers to any human insulin precursor or analog thereof originating an insulin molecule, or related molecules showing the same biological activity as insulin.

The meaning of "biological activity" is the biological activity associated with insulin, as measured by tests known by those skilled in the art.

As used herein, "insulin precursors" include the allelic variations of insulin precursors and derivatives obtained through simple modifications of the amino acid sequence of an insulin product.

As used herein, the terms "leader sequence" or "signal sequence" are equivalent expressions and refer to amino acid sequences involved in the transport of a peptide linked thereto through the cellular membrane.

As used herein, the term "DNA construction" refers to an expression cassette and other DNA sequences.

In order to solve the above mentioned drawbacks and problems, the inventors have developed a new and inventive yeast strain expressing high quantities of a human proinsulin molecule. This yeast strain was obtained by a new and inventive process or method comprising the steps of sequentially transforming and re-transforming the yeast with two different and inventive DNA constructions. The proinsulin secreted into the medium by the new strain is an insulin precursor with its C peptide replaced by a sequence of two amino acids, whose purification into the active human insulin generates few contaminants, thus avoiding the trypsin-mediated transpeptidation steps without reducing the required industrial yields or production. Also, said DNA constructions was cloned in such a way as to avoid the step of removing the remaining amino acids of the signal peptide from the secreted proinsulin.

Using the strain and DNA construction of the present invention it is possible to obtain production levels of human insulin from 200 to 400 mg/liter of fermentation broth, such levels being considered very appropriate for industrial production.

The chain encoding the human insulin precursor gene has been obtained through synthesis, using the polymerase chain reaction.

The gene synthesis process has the advantage of taking a short time and also of allowing for the selection of the most frequently used codons by the selected expression host.

This process comprises the chemical synthesis of a group of oligonucleotides that forms the entire sequence of both DNA chains of the selected precursors. Subsequently, complementary oligonucleotides are paired. In order to prevent the problems associated with cross'hybridization events between the oligonucleotides, a PCR method was used, and the process was completed in only one day.

The first step consists in providing a central template. The oligonucleotides were placed in the center of the sequence to be constructed, the oligonucleotides being complementary to each other in their 3' ends, with a specific Tm for each pair of nucleotides.

Subsequently, after elongation by PCR, from the 3' End, a complete double-stranded chain was obtained.

An aliquot of the PCR mixture was employed in a second PCR event after the addition of the corresponding primers.

Subsequently, the process was continued with appropriate pairs of primers until the final product was obtained.

Once the DNA fragments encoding the human insulin precursor had been obtained, the fragments were inserted into vector pPIC9 (In vitro). After ligation, the recombinant vector was characterized by restriction enzyme assays. Some of the randomly taken recombinant vectors were sequenced according to the Sanger method using the Sequenace V 2.0. Kit The primers used for sequencing the 5'-3' strand were 5' AOX1 and factor α, while the 3' AOX1 primer was used for the 3'-5' strand, both primers being supplied by Invitrogen. The results of sequencing confirmed that, the proinsulin sequence in the vector was correct.

The newly formed vector was termed pPIC9-Ib (FIG. 1). The vector digested with the appropriate restriction enzyme formed two DNA fragments. The fragment containing the inventive DNA construction was used for transforming the methylotrophic yeast. Said DNA construction comprises a methanol responsive sequence represented by the AOX1 gene promoter element of a methylotrophic yeast, a DNA sequence encoding a signal sequence, a human insulin precursor gene, the transcription termination signal sequence of the AOX1 gene, and the HIS4 gene encoding histidinol dehydrogenase, all of them included between 5' and 3' ends of the AOX1 gene.

According to the invention, as it is well known by any person skilled in the art, any circular or linear integrative site-specific vector may be used for the transformation of the yeasts.

In the DNA construction according to the invention, any signal sequence permitting the proper exportation of the insulin precursor may also be used. Preferably, the MF α signal sequence of *S. cerevisiae*, which is a peptide made up of 13 amino acid residues—may be employed. The MF α signal sequence has a protease site determined by the sequence of amino acids Lys-Arg-Glu-Ala (DEQ ID NO:26) During the cloning process in pPIC9 of a human insulin precursor gene, this gene is preferably inserted into the Xho I site removing the -Glu-Ala-residues, whereby the starting insert of the human insulin gene is maintained immediately adjacent to the proteases removal site (FIG. 1). The cloning in Xho I site allows for the obtention of a precursor which is released into the culture medium without the remaining amino acids of the signal peptide, thus simplifying the steps of purification of human insulin.

There are several genes included in the methanol metabolism pathway in yeast. The expression of these genes is controlled by their regulatory 5' regions which are responsive to methanol and are known as promoters. Any of said regulatory 5' regions are appropriate for use as promoters in the DNA construction according to the invention. Examples of regulatory regions include, but are not limited to, the *Pichia pastoris* primary alcohol oxidase enzyme (AOX1) gene promoter, the secondary alcohol oxidase II enzyme (AOX2) gene promoter, the *P. pastoris* dihydroxyacetone synthase (DAS) gene promoter, the *P. pastoris* P40 gene promoter, the *P. pastoris* catalase gene promoter, and the glyceraldehyde P dehydrogenase GAP promoter. Preferably, the *Pichia pastoris* primary alcohol oxidase enzyme (AOX1) gene promoter may be used since it is highly efficient in providing high levels of expression. It will be apparent to any person skilled in the art that any of the promoters or regulatory regions selected are within the scope of the invention, the 5' regions being preferred, however, by reason of their capacity to respond to an alcohol-containing medium.

The 3' termination sequences of the DNA construction according to the invention are appropriate for terminating, polyadenylating and stabilizing the mRNA encoded by the insulin precursor gene. Termination sequences that are characteristic of methylotrophic yeast families, preferably termination sequences of *Pichia pastoris* 3', may be used.

The DNA construction also contains a selectable marker gene. For these purposes, any selectable marker gene can be used provided that the gene is functional in methylotrophic yeast including, but not limited to, any gene capable of providing a selected phenotype to the methylotrophic yeast, which allows for the positive selection of the yeasts transformed with the DNA construction of the invention. An appropriate marker is any system comprising a mutant auxotrophic *Pichia pastoris* host cell and the wild biosynthetic type gene complementing the defficiencies of the host. It is preferable to use the HIS4 gene encoding histidinol dehydrogenases and auxotrophic mutant cells.

A particular feature of the DNA construction of the invention used for transforming methylotrophic yeasts is that it can be inserted into the genome of the host yeast through homologous recombination with the 5' and 3' ends of the endogenous AOX1 gene of yeast, said endogenous gene being replaced by the DNA construction of the invention.

The DNA construction according to the invention can be inserted into any functional vector in bacteria (chimeric vector), wherein the vectors include selection markers and replication sites appropriate for the bacteria. These vectors can be of circular shape forming extra-chromosomal replication plasmids within the bacteria. Several copies of the inventive DNA construction may be incorporated into said vector.

The DNA constructions of the invention are used for transforming methylotrophic yeasts according to any standard method of yeast transformation. Examples of transformation methods include, but are not limited to, electroporation, spheroplasts, transformation with lithium chloride and transformation with PEG 1000; preferably, the spheroplast and electroporation methods. Transformation with the DNA construction can be carried out with the DNA construction arranged in linear or circular pattern. The DNA construction is directed to the target gene of the yeast genome by flanking sequences with enough homology with the target gene so that the DNA construction can be integrated into the site to which it is directed. In an additional embodiment of the invention at least one copy of the DNA construction according to the invention is integrated into the host genome in the correct orientation.

It is possible to employ any methylotrophic yeast strain. Examples of methylotrophic strains include, but are not limited to, the genera *Pichia, Torulopsis, Hansenula* and *Candida*. It is preferable to use the *Pichia pastoris* GS 115 strain (ATCC NO 20864), as this strain contains the mutated HIS4 gene, and therefore, it is HIS⁻.

Of all His⁺ transformants, integration of the DNA construction of the invention by replacement of the structural AOX1 gene of the GS115 strain genome occurs with a frequency of about 5% to 35%. The replacement event of the structural AOX1 gene of the yeast genome generates yeasts called Mut$^s$, which are sensitive to the use of methanol as a carbon source. Any expert in the art can understand that the DNA construction of the invention can also be integrated through one of its 5' or 3' ends within the AOX1 gene generating Mut$^r$ yeasts which are resistant to the use of methanol as a carbon source because they keep the functional AOX1 gene; the DNA construction could also be integrated into the yeast genome by recombination with the His yeast gene whose sequence is also present in the DNA construction of the invention, or the DNA construction can be integrated into several sites of the yeast genome without restricting the scope of the invention.

Subsequently, the clones transformed with the DNA construction of the invention are selected by any method known in the art but it is preferable to perfom replicate plating experiments which make it possible to distinguish between His⁺ Mut$^r$ clones and His⁺ Mut$^s$ clones. Alternatively, clones with the capability of production can be selected using electrophoretic gels and immunochemical techniques.

Each Mut$^s$ and Mut$^r$ clone selected by the above mentioned methods were sub-cloned and isolated as pure clones. From all the selected clones, those producing adequate quantities of the insulin precursor were selected. These selected clones were characterized and the number of copies of the DNA construction of the invention was determined. Several clones producing adequate quantities of the insulin precursor were detected, and some of them were Mut$^s$ while others were Mut$^r$.

Two of these clones were subjected to a second transformation event herein also called re-transformation.

Figure 2:
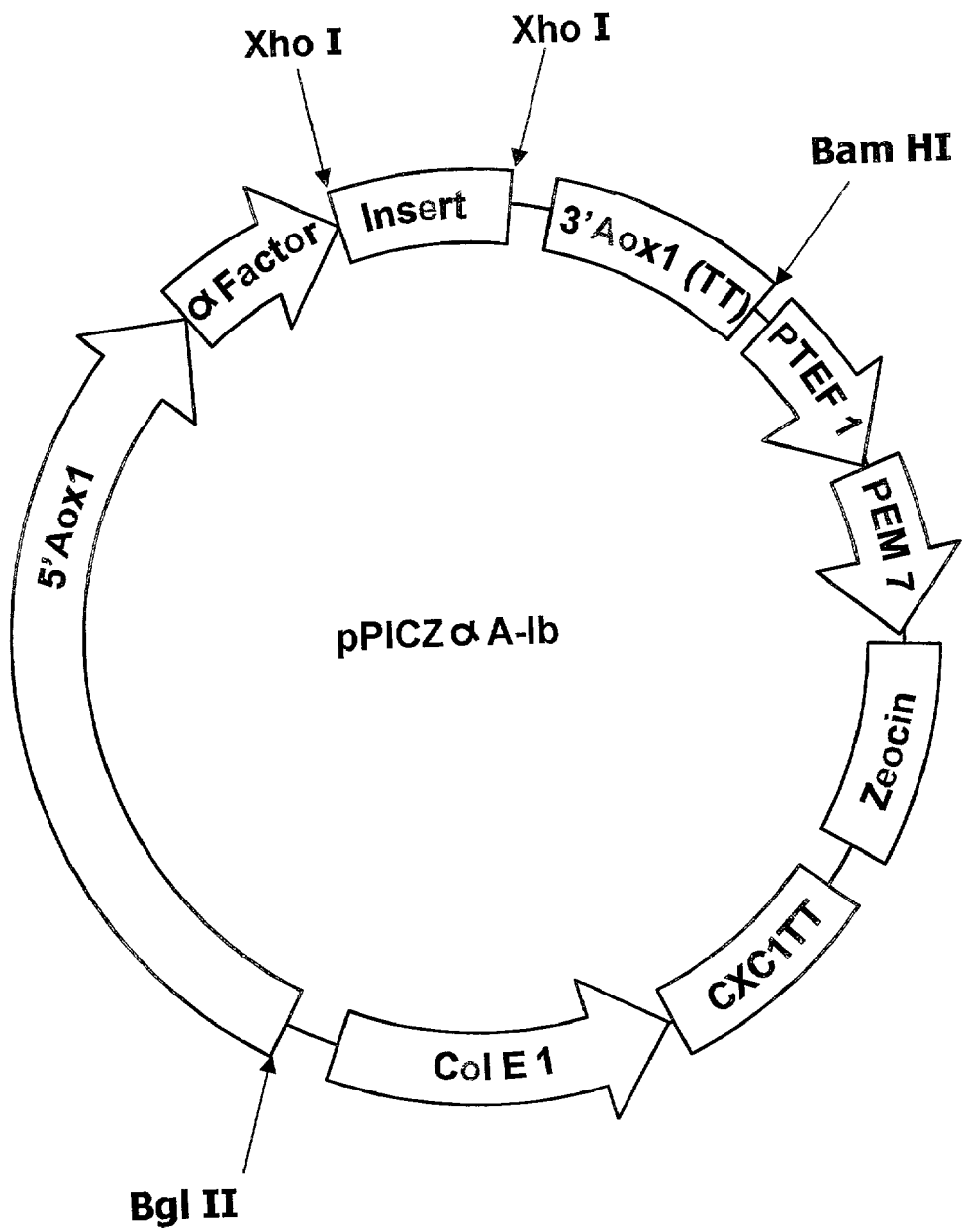
FIG. 2 shows a restriction map of plasmid pPICZαA-Ib.

In another embodiment of the invention, the nucleotide sequence encoding an insulin precursor was amplified by PCR, isolated and cloned in the pPICZαA vector in the especially designed multi-cloned site, thus obtaining a vector called pPICZαA-Ib (FIG. 2). Said vector contains a new DNA construction, called second DNA construction, comprising a promoter responsive to methanol of the methylotrophic yeast AOX1 gene; a DNA sequence encoding a signal sequence, the insulin precursor gene, a transcription termination signal sequence and a selection gene other than the ones used in the first DNA construction of the invention.

Any signal sequence which allows for the appropriate secretion of the insulin precursor may be employed. Examples of signal sequences include, but are not limited to, the MFα signal sequences of *s. Cerevisiae* and the signal sequence of alkaline phosphatase. It is preferable to use the MFα signal sequence of *s. cerevisiae*, corresponding to a peptide having 13 amino acid residues. During the cloning process of the gene encoding the insulin precursor in the pPICZαA plasmid, said gene was inserted into the Xho I site which eliminates (the -Glu-Ala-residues, whereby the insulin precursor gene was placed immediately adjacent to the protease removal site. With this cloning design the precursor released into the culture medium is free of residual amino acids of the signal peptide, thus avoiding one step in the purification sequence of human insulin.

Any 5' regulatory sequence can be used as a promoter in the second DNA construction of the invention. Examples of regulatory regions include, but are not limited to, the *Pichia pastoris* primary alcohol oxidase enzyme (AOX1) gene promoter, the secondary alcohol oxidase II enzyme (AOX2) gene promoter, the *P. pastoris* dihydroxyacetone synthase (DAS) gene promoter, the *P. pastoris* p40 gene promoter, the *P. pastoris* catalase gene promoter, and the glyceraldehyde P dehydrogenase GAP promoter. The preferred regulatory region is the *Pichia pastoris* primary alcohol oxidase enzyme (AOX1) gene promoter by reason of the high levels of expression obtained therewith. It will be apparent to any person skilled in the art that any of the selected promoters or regulatory regions are within the scope of the invention. The preferred 5' regulatory regions are capable of responding to a methanol-containing medium.

The 3' termination sequences of the second DNA construction according to the invention are appropriate for the termination, polyadenylation and stabilization of the mRNA encoded by the insulin precursor gene. Termination sequences that are characteristic of methylotrophic yeast families may be employed; preferably, Pichia pastoris 3' termination sequences are used.

The second DNA construction of the invention also contains a selectable marker gene. For these purposes any selectable marker gene functional in methylotrophic yeasts may be used, but it must be different from that used in the above transformation. The preferred marker gene is the zeocine gene which encodes for resistance to the zeocine antibiotic.

The new vector for re-transformation of the yeasts may comprise a single copy or multiple copies of the second DNA construction of the invention. Any method for obtaining a vector with multiple copies may be used, but the preferred method comprises a strategy for cloning multimers, which generates a vector with multiple copies of the second DNA construction of the invention, preferably containing from 2 to 18 copies of said DNA construction.

The new isolated recombinant vectors were characterized by analysis with restriction enzymes. The recombinant vectors were sequenced and the correct position within the vector of the sequence encoding the insulin precursor and the signal peptide were confirmed, as well as the number of copies of the gene of interest.

The new vectors were used for re-transformation of the yeasts. Vectors containing from 1 to 18 copies of the insulin precursor gene may be used. A preferred vector contains a single copy of the second DNA construction of the invention. Said recombinant vector may be linearized by digestion with a restriction enzyme or may be used in the circular form for re-transforming the yeasts cells. Preferably, the second transformation event in the $Mut^s$ clones obtained in the prior transformation step is carried out by said linearized vector.

Re-transformation may be carried out by method known in the art for the transformation of yeasts. These methods include, but are not restricted to, spheroplasts, electroporation, transformation with PEG 1000 and transformation with lithium chloride. The preferred methods are spheroplasts and electroporation.

Any person skilled in the art can understand that, vectors with single or multiple copies of the gene of interest may be employed in the second transformation event and wherein said retransformation step can be carried out by employing any method of yeast transformation without restricting or modifying the scope of the present invention.

The linearized vector with the DNA construction of the invention used for re-transforming the methylotrophic yeasts clones which produce the insulin precursor may preferably be capable of being inserted into the host genome in only one site, subsequently generating multiple genomic copies in vivo.

The re-transformed clones were appropriately selected by employing any of the known methods of double selection of yeasts. Preferably, double selection is carried out in a medium without histidine and with zeocine.

The selected positive clones were isolated and purified, and the sequences integrated into the yeast genome were characterized. The presence, in the total DNA, of re-transformed yeast clones of the DNA constructions of the invention were determined by the Southern blot method and by genomic analysis by PCR. The number of copies of the DNA construction of the present invention in the yeast genome was determined by the well-known Dot Blot method and analyzing the number of copies by PCR.

Among all the characterized clones the B1, 3.3 clone deposited on Jul. 25, 2000 in the American Type Culture Collection (ATCC), P.O. Box 1549, Manassas, Va. 20108, under deposit number PTA-2260, was preferably selected, the clone containing a copy of the first DNA construction of the invention and 13 copies of the second DNA construction of the invention, wherein said clone is $Mut^s$, it is resistant to the zeocine and it can grow in histidine free medium.

Other isolated production clones were: C1,46 clone: of phenotype $Mut^r$, wherein the integration of the first DNA construction of the invention was in the His yeast gene, containing 5 copies of the DNA construction, and wherein said clone was transformed in a single transformation event; C2,7 clone: of phenotype $Mut^s$, containing a single copy of the DNA construction and where said clone was transformed in a single transformation event; clone 25; of phenotype $Mut^r$, containing 6 copies of the DNA construction, the integration of the construction was in the yeast AOX 1 gene, and where said clone was transformed in a single transformation event; clone V8,10.1: of phenotype $Mut^s$, with 8 copies of the second DNA construction of the invention generated in vitro, and where said clone appears after the re-transformation event of a clone containing at least one copy of the first DNA construction.

All the transformed and retransformed strains selected for their desired phenotypic and genotypic characteristics were grown in Erlenmeyer flasks. The colonies and strains of interest were selected to be grown in fermenting devices.

Large scale production of insulin precursors was performed using the typical methods and processes used for methylotrophic yeasts; preferably, fermentations were carried out growing the yeast strains in the first step in a medium containing an excess of a non inducing carbon source, such as glycerol. In this step, expression of the constructions of the invention with the gene encoding the human insulin precursor is totally supressed, with generation of an important biomass but without producing the gene of interest. Subsequently to this period of growth the cells were grown preferably under methanol restrictive conditions with or without another carbon source for inducing the expression of the desired gene contained in the DNA constructions of the invention. Said DNA constructions were capable of expressing the gene encoding a human insulin precursor as a response to methanol and were also capable of releasing or secreting significant amounts of precursor into the culture medium, being said amounts appropriate and sufficient to be used on an industrial scale.

The present invention will now be described with reference to certain examples which further illustrate but do not limit the invention.

EXAMPLES

Example 1

Construction of the Insulin Precursor

An insulin precursor was constructed by the Polymerase chain reaction (PCR), employing human codons:

PCR conditions were established as described in: A. Method for Synthesizing Genes and cDNAs by Polymerase Chain Reaction. Di Donato, Alberto et al. Analytical Biochemistry. 212:291–293; 1993, modifying the annealing temperature according to the Tm of each oligonucleotide.

Primers:
5'-TCACACCTGG TGGAAGCTCT CTACCTAGTG   SEQ ID NO:1:
TGCGGG -3':

5'-GGTCTTGGGT GTGTAGAAGA AGCCTCGTTC   SEQ ID NO:2:
CCCGCACACT AGGTA-3':

5'-TTTGTGAACC AACACCTGTG CGGCTCACAC   SEQ ID NO:3:
CTGGTGGAA -3':

5'-GCTGGTACAG CATTGTTCCA CAATGCCACG   SEQ ID NO:4:
CTTGGTCTTG GGTGT -3':

5'-CTAGTTGCAG TAGTTCTCCA GCTGGTAGAG   SEQ ID NO:5:
GGAGCAGATG CTGGTACAGC AT-3':

Final Product:
                                     SEQ ID NO:6:
                 5'-TTTGTGAACC AACACCTGTG

CGGCTCACAC CTGGTGGAAG CTCTCTACCT AGTGTGCGGG

GAACGAGGCT TCTTCTACAC ACCCAAGACC AAGCGTGGCA

TTGTGGAACA ATGCTGTACC AGCATCTGCT CCCTCTACCA

GCTGGAGAAC TACTGCAACT AG-3':
(complete insulin precursor)

Example 2

Construction of an Insulin Precursor by Polymerase Chain Reaction (PCR) Using the Codons Most Commonly Found in *Pichia pastoris*.

Primers:
5'-ACTTGGTTGA AGCTTTGTAC TTGGTTTGTG   SEQ ID NO:7:
GTGAAAGAGG TTTCTTCTAC-3'

5'-AGAAGTACAA CATTGTTCAA CGATACCTCT   SEQ ID NO:8:
CTTAGTCTTT GGAGTGTAGA-3'

5'-ACACTTGTGT GGTTCTCACT TGGTTGAAGC   SEQ ID NO:9:
TTT-3'

5'-TTACTCGAGT TAGTTACAGT AGTTTTCCAA   SEQ ID NO:10:
TTGGTACAAA GAACAGATAG AAGTACAACA
TTGTTC-3'

5'-CCGCTCGAGA AGAGATTTGT TAACCAACAC   SEQ ID NO:11:
TTGTGT -3'

The resulting product contains the following sequence:

SEQ ID NO:12:
              5'-TTTGTTAACC AACACTTGTG TGGTTCTCAC

TTGGTTGAAG CTTTGTACTT GGTTTGTGGT GAAAGAGGTT

TCTTCTACAC TCCAAAGACT AAGAGAGGTA TCGTTGAACA

ATGTTGTACT TCTATCTGTT CTTTGTACCA ATTGGAAAAC

TACTGTAACT AA-3'

The PCR conditions were identical to those in Example 1.
1—One twentieth part of the product from each PCR was employed as a template for the subsequent event.
2—The final PCR product was purified in a microspin S300 column (Amersham) and digested with the Xho I restriction enzyme.

The digestion product was ligated to the pPIC9 vector previously digested with the restriction enzyme Xho I.
3—A digestion with the Hpa I restriction enzyme was carried out in order to detect the recombinant clones and the correct orientation of the insert.

Example 3

Construction of Factor α Using the Codons most Commonly Found in *Pichia pastoris*

The nucleotide sequence corresponding to the leader sequence or signal peptide was cloned using the same method.

The primers were:
SEQ ID NO:13:
5'-CGCGGATCCA AACCATGAGA TTCCCATCTA TCTTCACTGC
TGTTTTGTTC GCTGCT-3'

SEQ ID NO:14:
5'-GTTTTGTTCG CTGCTTCTTC TGCTTTGGCT GCTCCTGTTA
ACACTACTAC TGAAGACGAA ACTGCTCA-3'

SEQ ID NO:15:
5'-ACGTCGAAGT CACCTTCCAA GTCAGAGTAA CCGATAACCG
CTTCAGCTGG GATTTGAGCA GTTTCGTCTT C-3'

SEQ ID NO:16:
5'-GATGAACAAC AAACCATTAT TAGTAGAGTT AGAGAAAGGC
AAAACAGCAA CGTCGAAGTC ACCTTC-3'

SEQ ID NO:17:
5'-CCGCTCGAGA GAAACACCCT CTTCCTTAGC AGCGATAGAA
GCGATAGTAG TGTTGATGAA CAACAAACCA TT-3'

The final product has the following sequence:

SEQ ID NO:18:
             5'-ATGAGATTCC CATCTATCTT CACTGCTGTT

TTGTTCGCTG CTTCTTCTGC TTTGGCTGCT CCTGTTAACA

CTACTACTGA AGACGAAACT GCTCAAATCC CAGCTGAAGC

GGTTATCGGT TACTCTGACT TGGAAGGTGA CTTCGACGTT

GCTGTTTTGC CTTTCTCTAA CTCTACTAAT AATGGTTTGT

TGTTCATCAA CACTACTATC GCTTCTATCG CTGCTAAGGA

AGAGGGTGTT TCTCTCGAGA AGAGAGAGGC TGAAGCA-3'

Cloning of the MFα and the insulin precursor with the most commonly used codons of *Pichia pastoris*:
1—The signal peptide pPIC9 was replaced by a signal peptide with *Pichia pastoris* codons. pPIC9 was digested with restriction enzymes BamHI y XhoI
2—The digested fragments were separated on 0,8% agarose gel and the 7780 bp fragment was recovered.
3—The PCR product SEQ ID NO:18 was digested with the same restriction enzymes used in 1 and was ligated to the fragment obtained in 2.
4—The vector obtained in 3 and the PCR fragment SEQ ID NO:12 were digested with XhoI, and subsequently they were ligated.
5—The recombinants with the correct orientation of the insulin precursor insert were detected using the HpaI.

Example 4

Cloning of an Insulin Precursor Gene in a pPIC9 Yeast Vector

The DNA fragment encoding the insulin precursor was amplified by PCR, employing as a template SEQ ID NO:6 obtained previously, and as primers the following sequences:

```
                                      SEQ ID NO:19:
5'-GGGATCCAT ATGCTCGAGA AAAGATTTGT GAACCAACAC CTGT
                                                 -3'.

SEQ ID NO:20:
5'-TTAGAATTCC CGGGTCTAGT TGCAGTAGTT CT-3'.
```

The resulting PCR product was purified using a DNA Clean Up System Kit (Promega), according to the manufacturer's instructions.

The JM-109 $E.$ $coli$ strain was transformed with vector pPIC9.

Subsequently, the plasmid DNA was removed by using the Wizard Plus Miniprep DNA Purification System Kit (Promega).

The vector and the insert were digested with Xho I and Eco RI and both molecules were ligated according to conventional protocols.

5 µl of the ligation product were used for transforming 100 µl of competent bacteria of Jm-109 $E.$ $coli.$ strain according to conventional protocols.

The DNA was recovered from the ampiciline-resistant colonies using the above disclosed method.

200 ng of DNA of each sample were digested with 5 U of Alw NI restriction enzyme or with 5 U of Xho I and Eco RI enzymes.

The colonies containing the recombinant plasmids were grown and the plasmid DNA was recovered and purified.

Subsequently, the plasmid DNA was sequenced. The primers employed in the sequencing of the 5'-3' strand were: 5' AOX1 and α-Factor. The 3'-5' strand was sequenced by means of primer 3' AOX1 (sequences provided by the Invitrogen Kit, and designated 3'AOX1, 5'AOX1 and α-Factor.

The DNA required for this sequence was purified with a miniprep SV Kit (Promega). 3–5 µg of DNA were employed for each sequencing and the protocol was that suggested by the Amersham Kit.

Example 5

Cloning Strategy for an Insulin Precursor in a pPICZαA Yeast Vector.

This example illustrates the cloning of a copy of a gene encoding a human insulin precursor in pPICZαA.

The selected vector is pPICZαA, the general map thereof being shown in FIG. 2. This vector has 2 XhoI sites, one located in the multiple cloning site (1185) and the other in position 1247. The vector was digested with XhoI and the gene of interest was cloned according to the following protocol:

| PPICZαA | 10 µl |
|---|---|
| | (≈2 µg) |
| Neb2 (10x) Buffer | 4 µl |
| H₂O | 23.6 µl |

-continued

| BSA (100 X) | 0.4 µl |
|---|---|
| Xho I | 2 µl |
| | (40 U) |

Digestion was carried out at 37° C. for 6 hours. 40 µl of digestion product were loaded into a HR S-200 microspin column (Amersham).

Subsequently, dephosphatation was carried out with intestinal alkaline phosphatase or CIP according to the following protocol:

| pPICZαA (digested) | 40 µl |
|---|---|
| NebCIP (10x) buffer | 5 µl |
| H₂O | 4 µl |
| CIP | 1 µl |

The reaction was carried out at 37° C. for 30 minutes. Finally, the reaction was stopped by heat (75° C. for 10 minutes) and the DNA was purified by applying the sample into a microspin HR S-400 column.

Insert Preparation

The insulin precursor was amplified by PCR using the same conditions as in example 4 corresponding to the cloning of this sequence in vector pPIC9 with the following primers:

```
                                      SEQ ID NO:19:
5'-GGGGATCCAT ATGCTCGAGA AAAGATTTGT GAACCAACAC
CTGT-3'

SEQ ID NO:21:
5'-TCACTCGAGC GGTCTAGTTG CAGTAGTTCT-3'
```

50 µl of PCR product were purified in a microspin HR S-200 column. The product was digested for 6 hours according to the following protocol:

| PCR products | 40 µl |
|---|---|
| | (≈600 ng) |
| Neb2 (10 X) Buffer | 5 µl |
| H₂O | 3 µl |
| BSA (100 X) | 0.5 µl |
| Xho I | 1.5 µl |
| | (40 U) |

Digestion was stopped by heat (65° C., for 20 minutes) and the digestion products were purified in a microspin HR S-200 column.

Ligation of the insulin precursor fragment to the pPICZαA vector was carried out according to the following protocol:

The vector and the insert were digested with Xho I and were again quantified prior to ligation. Ligation was carried out with 100 ng of vector in each event, using the following molar relations of vector/insert 1:1, 1:3, 1:6 and 1:0 (negative control).

Top 10 strain of $E.$ $coli$ bacteria (Invitrogen), was transformed with 5 µl of each of the above mentioned ratios.

Thirteen colonies were obtained on the plate corresponding to ratio 1:3, while 6 colonies were obtained in the negative control. Said thirteen colonies were picked in tubes with 1,5 ml of LB medium for preparing conventional minipreps.

The resulting DNAs were digested with restriction enzyme AlwNI to determine the number and orientation of the resulting recombinants.

Seven recombinant colonies were obtained, 2 in the correct orientation, thus resulting in vector pPICZαA Ib (FIG. 2).

The DNA of one of the colonies was used for transforming the TOP10 strain.

Example 6

Multimeric Cloning Strategy of a Human Insulin Precursor in a Yeast Vector.

This example describes a method for obtaining a multi-cassette containing multiple copies of the gene encoding an insulin precursor in the vector pPICZαA Ib obtained in Example 5.

The process used to obtain the construction with two copies of the gene of interest is described below as an in vitro multimeric generation protocol according to the detailed instructions provided by the manufacturer (Invitrogen):

Two digestions were carried out:
Digestion 1: pPICZαA Ib with Bam HI
Digestion 2: pPICZαA Ib with Bam HI and Bgl II.

The expression cassette was recovered from an agarose gel.

The Bgl II-BamHI cassette, containing a copy of the insulin precursor gene was ligated with the product from digestion 1, and the Top 10 strain of E. Coli bacteria was transformed.

The plasmid DNA was extracted and the presence of recombinants was analyzed by restriction mapping.

The two types of configurations were differentiated by restriction mapping with Bgl II and Bam HI. The direct tandem configurations were chosen to continue the process. A vector designated pPICZαA Ib2 was generated using this process, with compatible Bgl II and Bam HI ends for ligation. However, both sites were destroyed when ligated.

The in vitro multimeric generation protocol was employed again, but replacing vector pPICZαA Ib for vector pPICZαA Ib2, thus obtaining vector pPICZαA Ib4 (vector with 4 copies of the gene in direct tandem).

Finally, a vector pPICZαA Ib8 was generated with the prior protocol by replacing vector pPICZαA Ib for vector pPICZαA Ib4.

To obtain the BglII-BamHI cassette, 4 μg of DNA were digested with both enzymes simultaneously, at 37° C., overnight. Subsequently, a gel was run with 0.8% agarose (Promega), such that the cassette was separated with the multimers of the remaining vector. To purify the DNA fragment from the agarose, the corresponding band of the gel was cut out and it was purified according to the Promega Clean-up Kit protocol.

The recombinant clones were always detected with the ALwNI enzyme.

Example 7

Yeast Transformations

The strain selected for transformation was *Pichia pastoris* GS115 (His4) (Invitrogen)

The transformation process was carried out according to the protocols of the instruction manual (*Pichia* expression Kit; version G161219, 250043) provided by Invitrogen.

Spheroplasts Transformation Process:

100 ul of spheroplast preparation (disclosed by Invitrogen) were used for each transformation event, and 10 ug of DNA (pPIC9-Ib) were added to the preparation. This preparation was incubated for 10 minutes at room temperature. During incubation, 1 ml of 1:1 PEG/CaT solution was added to the cell and DNA solution. This preparation was homogenized and incubated for 10 minutes at room temperature.

After a centrifugation step at 750×g for 10 minutes, the cellular pellet was re-suspended in 150 ul SOS medium and was kept for 20 minutes at room temperature. Then, 850 ul of 1M sorbitol were added and the cells were plated on agarose.

Several volumes (100–300 ul) of spheroplasts transformed with 10 ml of RD molten agarose were mixed and poured over plates containing RDB medium. Each sample was made by duplicate.

The plates were incubated at 28–30° C. for 4–6 days. Samples were taken and cellular viability was determined by growing the yeast cells in a RDHB medium containing histidine.

Example 8

Selection and Isolation of Recombinant Yeasts

The transformation of *Pichia pastoris* GS115 yeast strains with vector pPic9 digested with Bgl II promotes the recombination in locus AOX I. Replacement of the structural alcohol oxidase (AOX 1) gene occurs with a frequency of 5–35% of the His$^+$ transformants.

A plate replication experiment on minimum medium containing dextrose (MD) and minimum medium containing methanol (MM), was used to distinguish transformants Mut$^+$ and Mut$^s$.

His$^+$ colonies from the transformation of example 7 were selected according to the following protocol:

Each colony was picked with a sterile tip and applied to a MM plate by marking or streaking, and then to a MD plate.

In order to differentiate both phenotypes the corresponding controls for GS115/His$^+$ Mut$^+$ and GS115/His$^+$ Mut$^s$ (Invitrogen) were included.

The plates were incubated at 30° C. for 48–72 hours. By this method it is possible to identify the clones Mut$^s$ as well as those Mut$^r$ that normally grow on plates MD and MM.

Each of the clones Mut$^s$ and Mut$^r$ selected using this method was purified and pure clones were isolated. Isolation was carried out by making streaks of each colony on a minimum medium lacking histidine.

Example 9

Re-Transformation of Yeast Clones Obtained in Example 8

Re-transformation of clones was carried out using the electroporation transformation method according to the protocol suggested by Invitrogen. The DNA used in the transformation corresponds to 20 μg of plasmid pPICZαA Ib.

Example 10

Identification and Isolation of Colonies Producing Insulin Precursor, Retransformed as in Example 9.

After retransformation, the presence of clones producing the insulin precursor was revealed by means of an immunochemical method.

Aliquots of 50 to 600 ul of transformed cells were spread on plates containing YPDS agar medium with 100 ug/ml Zeocine.

Once the colonies resistant to Zeocine were grown, the presence of the insulin precursor was detected according to the following scheme:

On each plate under analysis a nitro cellulose membrane was placed in such a way that the membrane was in contact with each of the colonies and it was also applied as an inverted form onto the culture plates containing BMMY/agarose medium.

The plates were incubated with the filters attached for 24 hours at 30° C.

Then, the membranes were removed and subjected to a series of washes with a solution of 0.05% to 0.1% PBS/Tween-20 for an hour, changing the medium regularly.

The nitrocellulose membranes were blocked with 5% skimmed milk in 0.1% PBS/Tween-20 for 1 hour at 4° C.

Subsequently, the membranes were incubated with a Guinea pig anti-human insulin polyclonal antibody for one hour at room temperature, and then washed with 0.1% PBS/Tween-20 solution for 30 minutes.

Subsequently, the filters were incubated with a Guinea pig anti-IgG polyclonal antibody conjugated with peroxidase for 1 hour at room temperature and the filters were washed with a 0.1% PBS/Tween-20 solution for 30 minutes. Finally, the presence of peroxidase was revealed with 0.012% $H_2O_2$, 0.08% DAB; 100 mM Tris/ClH, pH 7.5.

The resulting positive colonies were identified and isolated from the original plate.

Based on the comparison of the reaction intensities, the high yielding clones were selected.

Example 11

Expression of the Recombinant Clones

In order to determine the productivity of the selected colonies, growing and induction experiments with BMGY/BMMY media were carried out. The first culture medium contains glycerol as the carbon source used by the microorganism for producing biomass. The second culture medium contains methanol which is the inductor of AOXI promoter.

The colonies were grown in Erlenmeyer flasks in a BMGY medium at 30° C. until an $OD_{600nm}$: 6–20 was reached. Then, the cells were centrifuged in order to replace the culture medium using BMMY in a volume corresponding to a fifth of the volume used in the growing phase. Culturing was continued for 120 hours after the medium change at a temperature of 30° C. with stirring. Every 24 hours 0.5% v/v 100% methanol was added and samples were taken to be evaluated by electrophoresis on 15% polyacrylamide, Tris/Tricine gel. Each sample was centrifuged to remove the cells, and the supernatant was treated with a sample buffer according to the protocols provided by (Laemmli, U.K. *Nature* 227:680–685; 1970).

Clones capable of secreting a peptide with an electrophoretic motility consistent with that of the insulin precursor having a PM from 5,800 to 5,900, were selected from the polyacrylamide gels.

The selected clones showed a very high protein expression. Thus, molecular characterization of the genome of said clones was performed.

Example 12

Molecular Characterization of Recombinant Clones

The extraction of *Pichia pastoris* DNA was carried out according to the method suggested by the Invitrogen guide.

Southern Blot Analysis

The Southern Blot analysis was carried out according to the standard protocol.

Briefly, an AOX probe which is a fragment of 871 bp of the AOX1 promoter obtained from the digestion of vector pPICZαA with enzymes BglII and HindI was used. The His probe, a fragment of 1587 pb of the HIS4 gene obtained by digestion of vector Ppic9 with the MscI; and the Ins probe which is a fragment of 227 pb obtained by PCR employing as a template the plasmid PPIC9IB and the primers corresponding to the sequences SEQ ID: 19 and 20, were also used.

The chromosomal DNA was digested with the BglII enzyme.

In filters hybridized with the AOX probe a band of about 1600 bp corresponding to AOX1 endogen gene was observed, not only for the non transformed GS115 yeasts but also for other Mut$^r$ clones. However, this band was not observed for Mut$^s$-transformed clones. In all transforming clones a band of 5700 bp corresponding to the expression cassette of insulin precursor under promoter AOX1 and the HIS4 gene was observed. This resulted from transformation with BglII-digested pPIC9-Ib, showing varying intensities depending on the number of inserted copies. In some clones, other bands with varying sizes were observed and these bands could correspond, for example, to BglII sites lost through exonucleolytic cleavage before insertion into the chromosome. In clones resulting from the retransformation of clone C2,7 with PPICZαA-Ib (clone B1, 3.3) (linearized with SacI) in addition to the band of 5.7 kbp, a band of 3.8 kbp corresponding to the insertion of the insulin precursor cassette under control of AOX1 promoter, and the zeocine gene was also observed.

Detailed Analysis of Each Clone Hybridized with the AOX Probe.

*Pichia pastoris* GS115: expected band of 1.6 kbp

Clone 25: expected bands of 1.6 and 5.7 kbp

Clone C1,46: expected bands of 1.6 and 5.7 kbp plus 3 bands of 7.8; 7.3 and 4.8 kbp.

Clone C2,7: expected band of 5.7 kbp. Lacks band of 1.6 kbp, indicating that this is a Mut$^s$ transformant.

Clone B1, 3.3: band of 5.7 kbp (insertion of C2,7) plus band of 3.8 kbp corresponding to insertion of pPICZαAIb cassette (linearized with SacI).

The same filters used with the AOX probe were re-hybridized with the HIS probe. A band of 2.7 kbp corresponding to endogenous HIS4 gene was observed, not only in the non transformed yeasts GS115 but also in most of the transforming clones. This band was not observed in clone C1,46 indicating in this case that there was an integration at the level of this gene whereby the BglII sites were lost. In all the transforming clones a band of 5700 bp was observed corresponding to the insulin precursor cassette under the AOX1 promoter and a HIS4 gene resulting from the transformation with BglII-digested pPIC9-Ib, showing varying intensities depending on the number of incorporated copies. In some clones, other bands of varying sizes were observed, for example bands corresponding to the loss of BglII sites through exonuclease digestions prior to insertion into the chromosome.

By the analysis of the Southern Blots hybridized with the HIS probe, a clone with only one copy of the expression cassette was individualized which was then taken as a pattern for the further determination of the number of copies in other clones.

By hybridization of the membranes with the insulin probe it was confirmed that all the bands obtained by hybridization with AOX and HIS probes except those corresponding to the endogenous genes, contained the gene corresponding to the insulin precursor.

Dot Blot Analysis

In order to determine the number of copies in the sequence of the insulin precursor of the different transforming clones, the Dot Blot technique was employed, using Ins and Gap probes. The Gap probe was used as a single copy gene pattern in all the clones. The number of copies of insulin was determined on the basis of the relation between the signals obtained with each probe and using the insulin single copy clone as a reference (obtained by Southern Blot Analysis), The number of copies of the gene encoding the insulin precursor in each clone was the following:

Clone 25: 6
Clone C1, 46: 6
Clone C2, 7: 1
Clone B1, 3.3: 13
Clone V8, 10.1: 8

Characterization of Mut$^s$ or MUt$^r$ colonies by PCR:
A protocol according to the following scheme was used:

| | |
|---|---|
| Chromosomal DNA: | 10–20 mg |
| 5'AOX | 0.5 μM |
| 3'AOX IN | 0.5 μM |
| dNTP | 0.2 mM |
| C12Mg | 1.5 mM |
| Taq: | 2 U |
| Buffer 10X | 1x |

Sequence of primers:

5' AOX I:   5'-GACTGGTTCC AATTGACAAG C
            (SEQ ID NO:25)

3' AOX IN:  5'-GTCGTGGTTT CTCATAGTAG AGTGGACA
            (SEQ ID NO:22)

The reaction conditions were the following: Denaturalization 94° C. 2 minutes. 1 cycle
25 cycles:
Denaturalization 94° C., 1 minute.
Annealing 55, 1 minute.
Extension 72° C., 1 minute.
Final extension: 72° C., 7 minutes. 1 cycle
A band of 730 bp was observed in Mut$^r$ clones. No band is observed in Mut$^s$ clones.

Quantification of the Number of Copies of the Insulin Precursor Gene by PCR in the Recombinant Colonies.

DNA was extracted from all the samples and the quantity was normalized by means of PCR with Gap primers (glyceraldehyde 3-phosphate dehydrogenase, single copy gene).

A new PCR was carried out with insulin specific primers according to the prior quantification, using increasing concentrations of templates for each point. In this way, saturation of the signal was avoided.

The PCR product was analyzed on a 2% agarose gel and after staining with ethidium bromide the bands were visualized with a Fotodyne imaging equipment. Quantification was carried out with ImageQuant software.

Clone C2,7 was selected as a unit, which has a single copy of the insulin precursor gene while the remaining clones were compared according to the intensity of the PCR products.

In order to make sure that the experimental conditions of the amplifications of the Gap genes and insulin were equivalent, primers with a similar hybridization T° and similar sizes were designed.

Gap primers:

Gap5':   5' GGT CAT CAC TGC TCC AT
         (SEQ ID NO:23)

Gap3':   5' AGC AGC ACC ACC AGT GGA AGA
         (SEQ ID NO:24)

PCR conditions:
Denaturalization: 94° C., 3 minutes
24 cycles of:
94° C., 1 minute
56° C., 1 minute
72° C., 30 seconds
Chromosomal DNA: 0, 5–1,5 NG
Gap primers 5': 0, 5 μM
Gap 3': 0, 5 μM
dNTP: 0, 2 mM
ClMg: 1, 5 mM
Taq Pol: 2, 5 U
Buffer 10×: 1×

The conditions for the insulin precursor were the same as described above for the specific primers.

Insulin precursor primers:

SEQ ID NO:19:
5'-GGGGATCCAT ATGCTCGAGA AAAGATTTGT GAACCAACAC
CTGT

SEQ ID NO:21:
5'-TCACTCGAGC GGTCTAGTTG CAGTAGTTCT

The results from the Dot Blot and quantitative PCR experiments were consistent, in other words, the same number of copies of recombinants was found in both methodologies.

Example 13

Fermentation Process

Fermentation was carried out not only in a BioFlo 3000 (New Brunswick Scientific) but also in a Biostat II (B.Braun Biotech) fermentor. Both fermentors are provided with 2,5 liter vessels. However, the fermentation process may be adapted to greater volumes.

Culture Preparation

The pre-culture for inoculating the fermentor was carried out in 125 ml Erlenmeyer flasks with 25 ml of BMGY culture medium, which was inoculated in the corresponding strain from frozen samples in 50% glycerol at −80° C.

The culture was incubated at 30° C., 240 r.p.m. for 14 hours in an orbital shaker.

Fermentation

The entire volume of 25 ml was transferred to the fermentor containing 1.2 L of BSM basal medium plus 4.35 ml/l of trace salts and 1% glycerol. The temperature was set to 30° C., dissolved oxygen at 35%, pH of 4.5 and aeration was of 1 vvm. Dissolved oxygen was controlled according to PID control of the stirring speed and addition Of $O_2$. The pH was controlled by automatic addition of a 28% ammonium hydroxide solution.

After approximately 16 hours of culture, or when the optic density reached a value close to 20 units of absorbance at 600 nm, the batch culture phase was completed.

The batch phase begun by feeding the fermentor with an additional 50% glycerol plus 12 ml/l of trace salts. The addition rate was regulated at 24 ml/l/h. This phase lasted approximately 20 hours, reaching values of OD of 300.

Once the growing phase of the biomass was completed, the cells were kept without feeding for half an hour and the production phase begun. During said phase pH was regulated from 3.5 to 5.5, and 100% methanol was added plus 12 ml/l of trace salts, at a rate of 1.2 ml/l/h. This last phase can be extended for up to 96 hours. Variations may be introduced by selecting adequate times for adding methanol to the culture, changing methanol concentration and using a double feed of glycerol/methanol, for further improving the production process.

After this step, the process is complete and the step of separating the cells from the culture broth is begun. When the fermentation process was carried out with high volumes, appropriate separation methods were used.

The implementation of this fermentation protocol in 1 and 100 liters allowed for the obtention of 200 to 400 mg of insulin precursor per liter of fermentation according to the amount of methanol employed for the induction.

The supernatant was appropriate for the first step of the purification of the insulin precursor.

Example 14

Purification of Recombinant Human Insulin Capturing the Precursor

Recovery of the recombinant human insulin precursor from the culture medium was carried out by cation exchange chromatography, for example, SP Sepharose Fast Flow (Pharmacia) (Katsoyannis, P. G., et al. *Biochemistry* 6:2642–2655; 1967) or by means of another adsorptive chromatographic technique, such as for example Hydrophobic Interaction Chromatography using a Phenyl Sepharose Fast Flow resin, according to the protocols disclosed by Gagnon, Pete et Al. Large Scale Process Development for Hydrophobic Interaction Chromatography, Part 1: gel Selection and Development of Binding Conditions. BioPharm 8:21–29; 1995.

The washing Buffer consisted of a solution of 50 mM sodium acetate and 50 mM NaCl, and the elution buffer consisted of 50 mM sodium acetate and 450 mM NaCl. The precursor was maintained soluble by the addition of ethanol or urea.

During the process, the column was balanced by 3 Vc of washing buffer at a lineal rate of 100 cm/h. Binding of the product was carried out at a linear rate of 90 to 120 cm/h. Once this step was completed, the product was rinsed with 4 Vc of washing buffer. The product was eluted with 10 Vc of eluting buffer. The chromatographic process was monitored by OD at 280 nm. Those fractions containing the product of interest were collected in a single solution.

Enzymatic Processing of the Insulin Precursor Digestion with Trypsin and Carboxipeptidase B The digestion was carried out by adjusting the concentration of the precursor solution from 1 to 20 mg/ml, as disclosed in the European Patent NO EP 195691. The reaction progress was monitored by RP-HPLC. Digestion was stopped with 7.5 M acetic acid.

Proteases were removed from the reaction medium by molecular exclusion (chromatography or ionic exchange chromatography at pH: 2–5). The fractions corresponding to the digested precursor were collected in a single solution for its further digestion with carboxipeptidase B according the European Patent EP 195691.

As an alternative method, the simultaneous addition of both enzymes was carried out following the protocols disclosed in the European Patent EP 195691 and in the publication Lila R. Castellanos-Serra et Al. *FEBS Letters* 378: 171–176; 1996.

Final purification of the insulin resulting from the enzymatic action can be carried out by any chromatographic technique such as the ones disclosed in U.S. Pat. No. 5,663,291; EPO NO 195691; and the techniques disclosed in the publication of Kroeff; Eugene et Al. Journal of Chromatography. 461:45–61: 1989.

While preferred embodiments of the present invention have been illustrated and described, it will be evident to those skilled in the art that various changes and modifications may be made therein without departing from the scope of the invention as defined in the appended claims.

I claim:

1. A yeast strain, wherein the strain is yeast *Pichia pastoris* deposited under accession number ATCC PTA-2260.

* * * * *